United States Patent
Strunak

(10) Patent No.: US 6,758,666 B1
(45) Date of Patent: Jul. 6, 2004

(54) CANDLE TOPPER

(76) Inventor: John J. Strunak, 107 Willow St., Schuylkill Haven, PA (US) 17972

( * ) Notice: Subject to any disclaimer, the term of this patent is extended or adjusted under 35 U.S.C. 154(b) by 0 days.

(21) Appl. No.: 10/442,150

(22) Filed: May 21, 2003

(51) Int. Cl.[7] ................................................ F23D 3/16
(52) U.S. Cl. ..................... 431/291; 431/126; 362/161
(58) Field of Search ................................ 431/291, 126, 431/125; 362/161; D26/23

(56) References Cited

U.S. PATENT DOCUMENTS

| | | | | |
|---|---|---|---|---|
| 396,252 | A | * 1/1889 | Beidler | 40/540 |
| 589,173 | A | * 8/1897 | Henke | 40/441 |
| 1,490,341 | A | 4/1924 | Olney | |
| D71,848 | S | 1/1927 | Nist | |
| 2,214,991 | A | * 9/1940 | Candy, Jr. | 362/161 |
| 2,842,658 | A | * 7/1958 | Reachi | 362/161 |
| D304,226 | S | 10/1989 | Kim et al. | |
| 5,055,035 | A | * 10/1991 | Hancovsky | 431/291 |
| D337,103 | S | 7/1993 | Harper | |
| 5,683,239 | A | * 11/1997 | Cardosi | 431/291 |
| D425,636 | S | 5/2000 | Freeman | |
| D436,866 | S | 1/2001 | Freeman | |
| D449,529 | S | 10/2001 | Poppick | |
| D462,132 | S | 8/2002 | Papai | |
| 6,663,384 | B2 | * 12/2003 | Papai | 431/289 |

* cited by examiner

Primary Examiner—Alfred Basichas
(74) Attorney, Agent, or Firm—Richard C. Litman

(57) ABSTRACT

A candle topper with a solid base in the shape of a polygonal lampshade with a top, a bottom and a center. A crown is on the top of the solid base for grasping the candle topper; a fitted bottom piece is attached to the bottom of the solid base, that is tapered and fitted to place on top of a corresponding candle and container. The solid base has a hole bored out at its top and center to form a hidden compartment that is covered with the crown, while the hidden compartment can be used for the storage of small items. The sides of the solid base can also be routed out to accommodate fitted photographs and dried flowers, which are covered and protected by thin transparent thermoplastic for ornamental purposes.

10 Claims, 4 Drawing Sheets

CANDLE TOPPER

BACKGROUND OF THE INVENTION

1. Field of the Invention

The present invention relates to a candle topper with desirable accessory features.

2. Description of the Related Art

Candle toppers have always been a popular craft item. These items are decorative in nature and are designed to be used with unlit candles. Candle toppers are used to prevent the scent from dissipating from the candle while the candles are in storage or display waiting to be sold. Candle toppers have been in existence for about as long as people have used candles. As would be expected, these ornamental items are also well documented and reflected in the related art.

U.S. Pat. No. Des. 71,848 issued to Nist, shows an ornamental design for a candle cap. U.S. Pat. No. Des. 304,226 issued to Kim et al, shows an ornamental design for a cover for jars of fragrance, jewelry or similar article. U.S. Pat. No. Des. 377,103 issued to Hibner et al., shows an ornamental design for a candle topper in the shape of a human face.

U.S. Pat. No. Des. 425,636 issued to Freeman, shows an ornamental design for a candle top cover. U.S. Pat. No. Des. 436,866 issued to Freeman, shows an ornamental design for a candle container top. U.S. Pat. No. Des. 449,529 issued to Poppick, shows an ornamental design for a jar lid. U.S. Pat. No. Des. 462,132 issued to Papai, shows an ornamental design of a containerized candle cover.

U.S. Pat. No. 1,490,341 issued to Olney, describes the use of an ornamental cover for designating the contents of a sealed container. For example, an ornamental cover with the shape of a strawberry on top of it would be used to seal a jar full of strawberry jam. There are also ornamental covers in the shape of a bunch of grapes and an apricot for grape jelly and apricot jelly.

Although a wide variety of candle topper shapes are shown and described in the previously discussed patents, what is really needed in the marketplace is a candle topper that has a plurality of useful supplemental features, such as providing a hidden compartment for the hidden storage of small valuable items such as paper money and jewelry. Such a candle topper would be of interest to many arts and crafts buyers who purchase and collect these items.

None of the above inventions and patents, taken either singly or in combination, are seen to describe the instant invention as claimed. Thus a candle topper solving the aforementioned problems is desired.

SUMMARY OF THE INVENTION

The invention is a candle topper with a solid base in the shape of a polygonal lampshade with a top, a bottom and a center. A crown is on the top of the solid base for grasping the candle topper; a fitted bottom piece is attached to the bottom of the solid base, that is tapered and fitted to place on top of a corresponding candle and container; the solid base has a hole bored out at its top and center to form a hidden compartment that is covered with the crown, while the hidden compartment can be used for the storage of small items. The sides of the solid base can also be routed out to accommodate fitted photographs and dried flowers, which are covered and protected by thin transparent thermoplastic for ornamental purposes.

Accordingly, it is a principal object of the invention to provide a candle topper that has a hidden compartment for storing valuable items.

It is another object of the invention to provide a candle topper that can display photographs and dried flowers on its exterior.

It is a further object of the invention to provide a more durable candle topper that does not easily break and shatter.

Still another object of the invention is to provide a candle topper that prevents the scent from a scented candle from dissipating.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
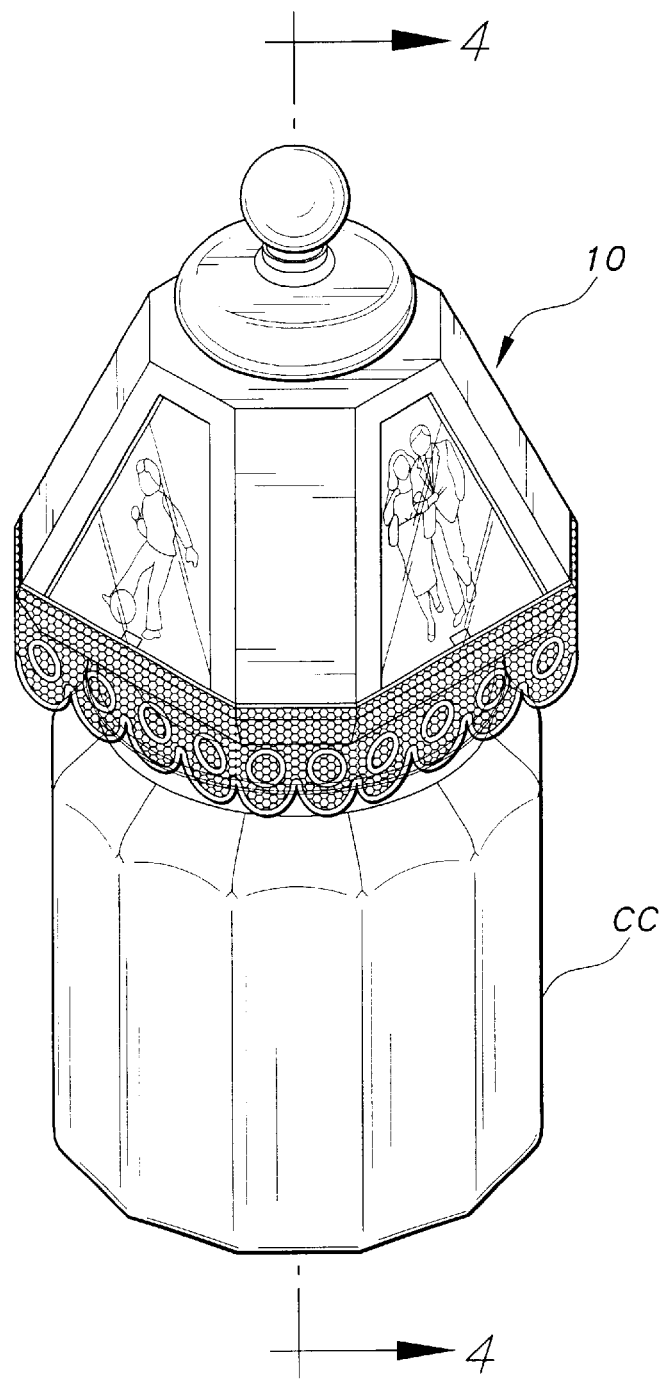
FIG. 1 is an environmental, perspective view of a candle topper according to the present invention.

The present invention is a candle topper 10 that can be used in combination with a corresponding candle and container CC, as is shown in FIG. 1.

Figure 2:
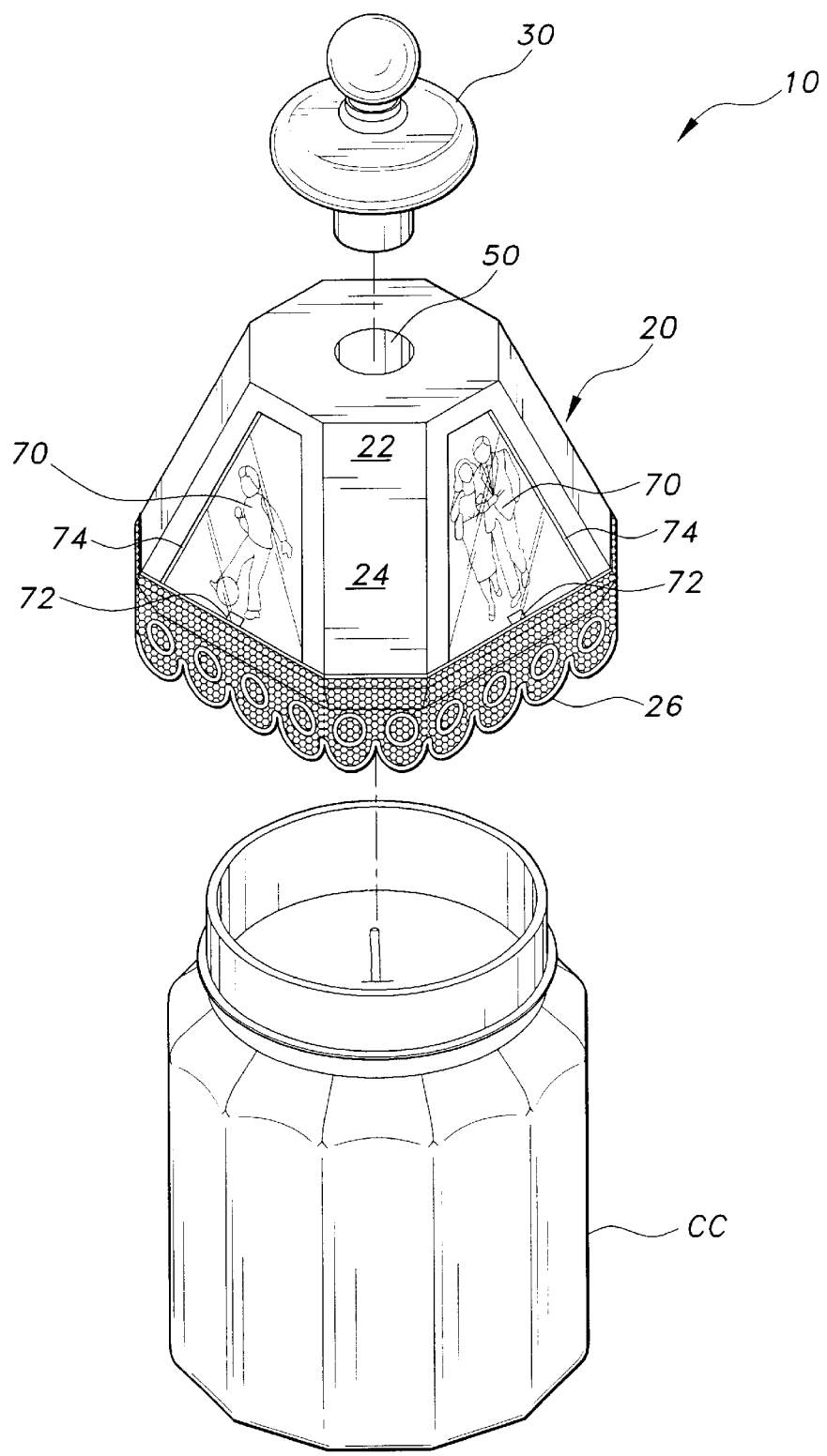
FIG. 2 is an exploded side perspective view of a candle topper according to the present invention.
Figure 3:
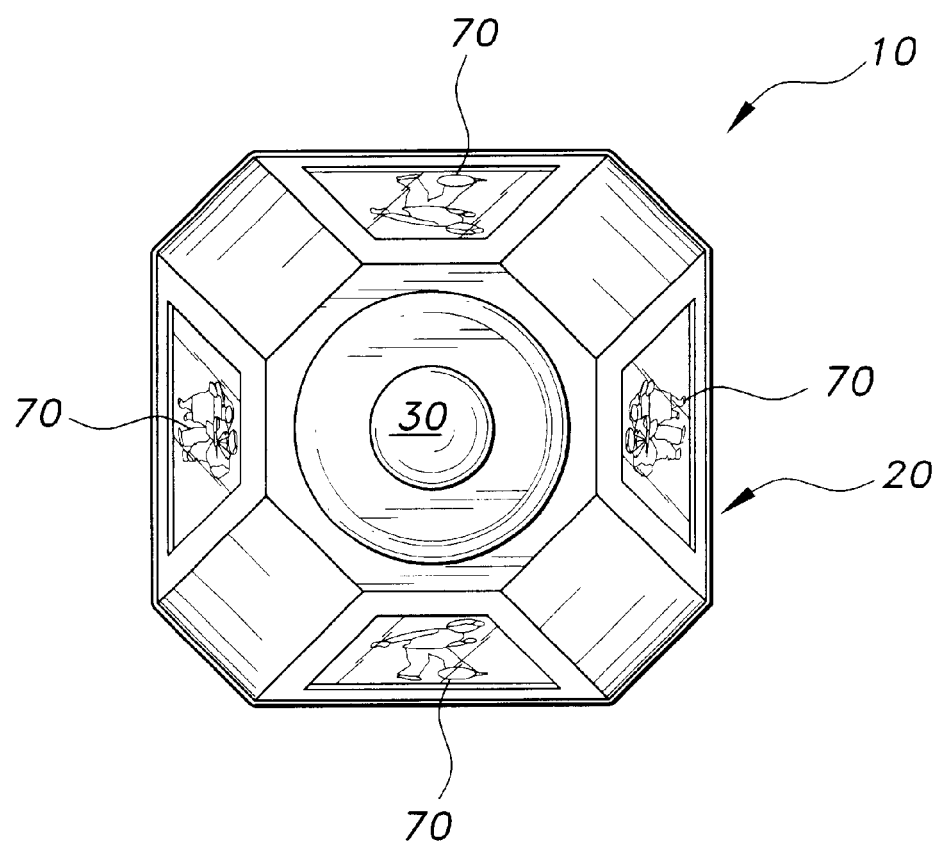
FIG. 3 is a top view of a candle topper according to the present invention.

As is shown in FIG. 2 and FIG. 3, the candle topper 10 comprises a solid base 20 in the shape of a polygonal lampshade with a top 22, a bottom 26 and a center 24. There is also a crown 30 on the top of the solid base 20 for grasping the candle topper 10 and a fitted bottom piece 40 (shown in FIG. 4) attached to the bottom 26 of the solid base 20, that is tapered and fitted to place on top of a corresponding candle and container CC. The solid base 20 has a hole 50 bored out at its top and center to form a hidden compartment 60 that is covered with the crown 30. The compartment 60 can be used for the storage of small items and the sides 70 of the solid base 20 can be routed out to accommodate fitted photographs and dried flowers, which are covered and protected by shaped thin transparent thermoplastic 74 for ornamental purposes.

The candle topper 10 can accommodate a fitted circular candle and container CC where the fitted bottom piece 40 is in the shape of a circle. The candle topper 10 can also accommodate a fitted square candle and container (not shown) where the fitted bottom piece 40 is in the shape of a square. The candle topper 10 is made of solid wood and will not break or shatter like comparable ceramic candle toppers if dropped. The candle topper 10 can also be used on votive and potpourri containers (not shown) as well as candles and containers CC, to prevent scent dissipation. The candle topper 10 gives an ordinary candle and container CC the illusion and decorative look of being a miniature lamp, which can be more aesthetically pleasing to look at than an ordinary candle and container CC.

Shaped photographs or small dried flowers can also be placed on the sides of the solid base 70. These fitted photographs or small dried flowers are placed in the routed sides of the solid base 70. Thin transparent thermoplastic 74 can then be fitted to the shape of the routed sides of the solid base 70 to protectively overlap the photographs or small dried flowers. A small notch 72 is also placed at the bottom of the thin transparent thermoplastic 74. This small notch 72 can be picked and pried off of the photographs or small dried flowers that are placed over the routed sides of the solid base 70 for easily changing any of the pictures or small dried flowers.

Figure 4:
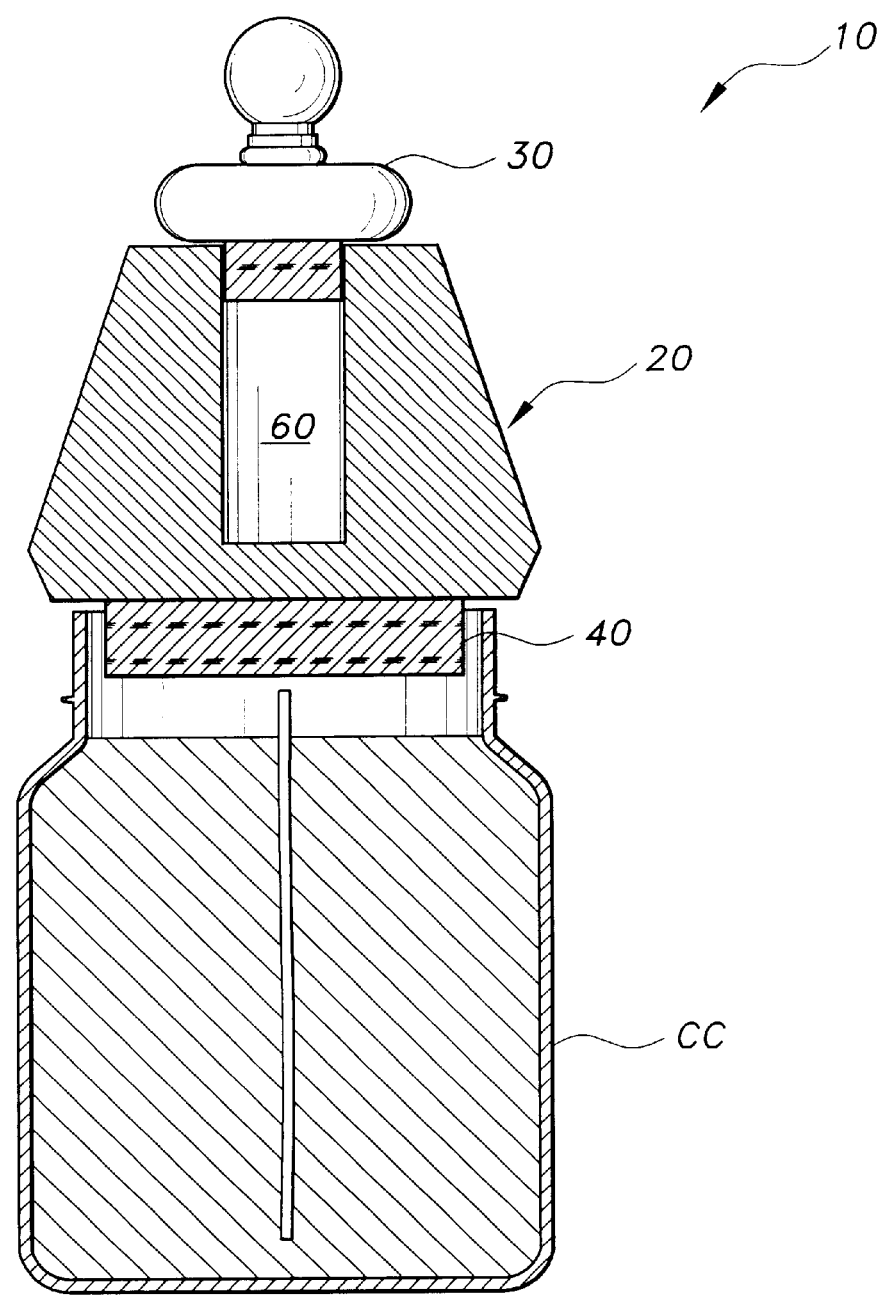
FIG. 4 is a cross sectional view along lines 4—4 of FIG. 1.

FIG. 4 best illustrates the hole 50 and hidden compartment 60 features of the candle topper 10. The hole 50 and hidden compartment 60 are provided on the top portion of the solid base 22 and center portion of the solid base 20. The hole 50 is centered to go approximately ¾ths of the way down through the entire depth of the candle topper 10. The hole 50 and the hidden compartment 60 are covered by the crown 30 of the candle topper 10, which also slightly extends down into the hole 50 for additional snugness and fit. The hole 50 and the hidden compartment 60 is large enough to hold and accommodate rolled up paper money or other types of small valuable items.

The candle topper 10 is made of solid wood and is approximately 3" in height, approximately 3" in width at the base of the lamp shade shape and approximately 3" long, when standing by itself. The fitted bottom piece 40 is based on the corresponding shape of the orifice of the candle and container CC. Typically, this shape is either round or square shaped, but it can be any shape to accommodate the orifice shape of the candle and container CC. As previously discussed, the candle topper 10 is not limited to use on only candles and containers CC, but can also be used to preserve the scent of various votive and potpourri containers.

Photographs as well as small dried flowers can be cut in the shape of the side of the candle topper 70 for decorative display and ornamentation. Overlapping thin transparent thermoplastic must also be cut to shape to accommodate the sides of the candle topper 70. The hole 50 and hidden compartment 60 is approximately ¾" in diameter and the fitted bottom piece 40 is made of cork that can be shaped to accommodate the orifice of a candle and container CC or other types of containers previously discussed.

It is to be understood that the present invention is not limited to the embodiment described above, but encompasses any and all embodiments within the scope of the following claims.

I claim:

1. A candle topper, comprising:
    a solid base having the shape of a polygonal lampshade with a top, a bottom and a center;
    a crown mounted on the top of the solid base for grasping the candle topper;
    a fitted bottom piece attached to the bottom of the solid base, the bottom piece being tapered and fitted to place on top of a corresponding candle and container;
    said solid base having a hole defined in the top and center to form a hidden compartment, the crown frictionally engaging the hole in order to cover the hole, said compartment being adapted for storage of small items;
    said sides of the solid base having recesses defined therein adapted for receiving fitted photographs and dried flowers; and
    a thin, transparent thermoplastic cover disposed over each of the said recesses.

2. The candle topper, according to claim 1, wherein the fitted bottom piece is in the shape of a circle.

3. The candle topper, according to claim 1, wherein the fitted bottom piece is in the shape of a square.

4. The candle topper, according to claim 1, wherein the thin transparent thermoplastic cover has a small notch on each side for easy removal.

5. The candle topper, according to claim 1, wherein the candle topper is made of solid wood.

6. A candle topper, used in combination with a corresponding candle and container, comprising:
    a container having an open mouth;
    a candle disposed in said container
    a solid base having the shape of a polygonal lampshade with a top, a bottom and a center;
    a crown mounted on the top of the solid base for grasping the candle topper;
    a fitted bottom piece attached to the bottom of the solid base, the bottom piece being tapered and inserted into the open mouth of said container to close the open mouth;
    said solid base having a hole defined in the top and center to form a hidden compartment, the crown frictionally engaging the hole in order to cover the hole, said compartment being adapted for storage of small items;
    said sides of the solid base having recesses defined therein adapted for receiving fitted photographs and dried flowers; and
    a thin, transparent, thermoplastic cover disposed over each of the said recesses.

7. The candle topper, according to claim 6, wherein the fitted bottom piece is in the shape of a circle.

8. The candle topper, according to claim 6, wherein the fitted bottom piece is in the shape of a square.

9. The candle topper, according to claim 6, wherein the thin transparent thermoplastic cover has a small notch on each side for easy removal.

10. The candle topper, according to claim 6, wherein the candle topper is made of solid wood.

* * * * *